United States Patent
Cies et al.

(10) Patent No.: US 10,874,789 B2
(45) Date of Patent: Dec. 29, 2020

(54) MEDICAL FLUID DELIVERY SYSTEM

(71) Applicants: DREXEL UNIVERSITY, Philadelphia, PA (US); NEW YORK UNIVERSITY, New York, NY (US)

(72) Inventors: Jeffrey John Cies, Pottstown, PA (US); Arun Chopra, Springfield, PA (US); Moses Noh, Ambler, PA (US)

(73) Assignees: DREXEL UNIVERSITY, Philadelphia, PA (US); NEW YORK UNIVERSITY, New York, NY (US)

( * ) Notice: Subject to any disclaimer, the term of this patent is extended or adjusted under 35 U.S.C. 154(b) by 279 days.

(21) Appl. No.: 15/780,280

(22) PCT Filed: Dec. 2, 2016

(86) PCT No.: PCT/US2016/064734
§ 371 (c)(1),
(2) Date: May 31, 2018

(87) PCT Pub. No.: WO2017/096238
PCT Pub. Date: Jun. 8, 2017

(65) Prior Publication Data
US 2018/0344916 A1    Dec. 6, 2018

Related U.S. Application Data

(60) Provisional application No. 62/262,841, filed on Dec. 3, 2015, provisional application No. 62/385,144, filed (Continued)

(51) Int. Cl.
*A61M 1/16*    (2006.01)
*A61J 1/10*    (2006.01)
(Continued)

(52) U.S. Cl.
CPC .............. *A61M 1/1668* (2014.02); *A61J 1/00* (2013.01); *A61J 1/10* (2013.01); *A61J 1/14* (2013.01);
(Continued)

(58) Field of Classification Search
CPC ........ A61J 1/10; A61J 1/00; A61J 1/20; A61J 1/2089; A61J 1/1481; A61M 1/1668
See application file for complete search history.

(56) References Cited

U.S. PATENT DOCUMENTS

| 3,788,369 A | 1/1974 | Killinger |
| 4,411,662 A | 10/1983 | Pearson |

(Continued)

FOREIGN PATENT DOCUMENTS

EP    00904763 A2    3/1999

*Primary Examiner* — Leslie R Deak
(74) *Attorney, Agent, or Firm* — Howson & Howson LLP

(57) ABSTRACT

An assembly for adding a medication or like substance to a liquid solution in a flexible bag (10) is provided. The flexible bag (10) contains a liquid solution, such as dialysate. An adapter (14) extends from the flexible bag (10) and includes a skirt (20) having an array of resilient sections (22) for engaging and snapping onto a neck finish (106) of a separate vial (100) containing a medication or like substance. A locking device (16) is adapted to be secured about the skirt (20) in a locking position that prevents outward movement of the array of resilient sections (22) and thereby prevents disengagement of the vial (100) from the adapter (14). A method of transferring the liquid solution from the bag (10) to the vial (100), mixing the medication with the liquid solution, and returning the mixture to the bag (10) is also provided.

13 Claims, 3 Drawing Sheets

Related U.S. Application Data on Sep. 8, 2016, provisional application No. 62/397,748, filed on Sep. 21, 2016.

(51) Int. Cl.
- *A61J 1/20* (2006.01)
- *A61J 1/14* (2006.01)
- *A61J 3/00* (2006.01)
- *A61J 1/00* (2006.01)

(52) U.S. Cl.
CPC .................. *A61J 1/20* (2013.01); *A61J 1/201* (2015.05); *A61J 1/2055* (2015.05); *A61J 1/2089* (2013.01); *A61J 3/00* (2013.01); *A61M 1/1666* (2014.02)

(56) References Cited

U.S. PATENT DOCUMENTS

| | | | |
|---|---|---|---|
| 4,560,382 A * | 12/1985 | Isono | A61J 1/10 604/408 |
| 4,607,671 A | 8/1986 | Aalto et al. | |
| 4,759,756 A | 7/1988 | Forman et al. | |
| 4,898,209 A | 2/1990 | Zbed | |
| 5,304,163 A | 4/1994 | Bonnici et al. | |
| 5,893,397 A | 4/1999 | Peterson et al. | |
| 6,875,203 B1 | 4/2005 | Fowles et al. | |
| 7,442,189 B2 | 10/2008 | Curutcharry | |
| 8,562,583 B2 | 10/2013 | Akerlund et al. | |
| 8,721,612 B2 | 5/2014 | Domkowski et al. | |
| 8,894,609 B2 | 11/2014 | Gobbi Frattini | |
| 8,905,994 B1 | 12/2014 | Lev et al. | |
| 2006/0172954 A1 | 8/2006 | Jensen et al. | |
| 2010/0237011 A1 | 9/2010 | Ross et al. | |
| 2011/0004143 A1 | 1/2011 | Beiriger et al. | |
| 2013/0053814 A1* | 2/2013 | Mueller-Beckhaus | A61J 1/2096 604/414 |
| 2013/0213891 A1* | 8/2013 | Karoor | A61M 1/28 210/646 |

\* cited by examiner

MEDICAL FLUID DELIVERY SYSTEM

BACKGROUND

In many instances, a medicine or like substance, which may be provided in a vial or like container, is required to be added to a fresh supply of a medical solution contained separately within a flexible bag, pouch, or like container before the medical solution is utilized during a medical treatment. An example of such a bag is a dialysate bag adapted for being connected to a dialysis machine or the like and for being utilized in dialysis treatment.

Dialysis is a life-support treatment for a patient suffering from kidney failure and may utilize a machine to filter harmful wastes, salt, and excess fluid from the patient's blood. Hemodialysis is a type of kidney dialysis in which blood is filtered using a dialyzer and dialysis machine, and peritoneal dialysis is a type of kidney dialysis in which blood is filtered inside the patient's body after the patient's abdomen is filled with a peritoneal dialysis solution.

During a hemodialysis session, for instance, blood flows from the patient via tubing through a special filter (a dialyzer) of the machine. As the blood flows through the filter, wastes and extra fluids are removed from the blood while permitting the blood to retain a proper balance of minerals, such as potassium and sodium. After the blood is cleaned by the dialyzer, it is returned to the patient's body via return tubing.

Dialysate is a fluid or solution used during dialysis that helps remove unwanted waste products from the blood and helps return electrolytes and minerals to their proper levels in the patient's body. Thus, during a dialysis treatment, fresh dialysate and blood flow through the dialyzer and impurities filtered out of the blood are transferred into the flow of dialysate. Thereafter, the dialysate containing unwanted waste products and excess electrolytes exit the dialyzer and is discarded.

A supply of fresh dialysate solution may be provided in a flexible bag or pouch (i.e., a so-called "dialysate bag") that may be connected to a dialysis machine or the like. In many cases, a medicine, such as an antibiotic, is added to the dialysate solution within the bag before the bag is attached to a dialysis machine or the like.

By way of example, a procedure for injecting an antibiotic provided in powdered form into a dialysate bag may include the following basic steps. A vial containing the antibiotic powder and a separate vial containing a solution to mix with the powder are provided and the stopper within the mouth of each vial is wiped clean. A syringe is used to penetrate the stopper and extract fluid from one of the vials and then penetrate the stopper and inject the fluid into the vial containing the powder. This may be repeated several times as needed. Thereafter, the vial containing the powder and injected fluid is shaken to mix the powder and fluid. A syringe is then used to extract the mixture from the vial and inject it into a port or stopper provided on the dialysate bag.

Complicating this conventional procedure is the necessity to perform the above discussed tasks in a separate clean room or IV room of a hospital or like treatment facility and not within the room in which dialysis treatment actually occurs. Thus, according to conventional practice, a fresh supply of dialysate contained within a bag is taken to a sterile IV room (i.e., a room in hospital or like facility for the sterile preparation of intravenous (IV) medications) where antibiotics are added to the dialysate bag. However, this may take approximately 20 minutes to up to 2 hours depending upon work load and available personnel within the IV room. The bag is ultimately returned to the nurse or other caregiver responsible for setting up the dialysis machine and only then may the dialysis treatment be started.

SUMMARY

According to an embodiment, an assembly for adding a medication or like substance to a liquid solution contained in a flexible bag, pouch or container is provided. The assembly includes the flexible bag, an adapter extending from and communicating with a port of the flexible bag, and a locking device. The adapter has a skirt for engaging about a neck finish of a separate vial containing a medication. The skirt comprises an array of spaced apart resilient sections that permit the skirt to expand about the neck finish when being applied to the vial and then resiliently return to a normal condition in which the neck finish is gripped by the skirt of the adapter. The locking device is then engaged about the skirt in a locking position such that outward movement or expansion of the array of resilient sections of the skirt is prevented by the locking device.

According to another embodiment, the assembly described above further includes a vial. Thus, the assembly includes a flexible bag containing a liquid solution, an adapter extending from the flexible bag, a locking device, and a vial containing a medication. The vial has a neck finish defining a mouth having a stopper. The adapter extends integrally from the flexible bag and has a skirt with an array of resilient sections for engaging and resiliently snapping onto the neck finish of the vial. The locking device can be secured about the skirt in a locking position that prevents outward movement of the array of resilient sections of the skirt and that thereby prevents disengagement of the vial from the adapter.

According to another aspect of the embodiment, a method of adding a medication or like substance to a liquid solution contained within a flexible bag, pouch or container is provided. An adapter connects the flexible bag containing the liquid solution to a separate vial containing the medication or like substance. The vial has a neck finish defining a mouth with a stopper, and the adapter extends integrally from the flexible bag, has a skirt with an array of resilient sections for engaging and resiliently snapping onto the neck finish of the vial. The adapter also includes a cannula which is positioned to pierce the stopper of the vial when the adapter is connected to the neck finish. After the adapter is connected to the vial, a locking device is placed in a locking position about the skirt such that the locking device prevents outward movement of the array of resilient sections of the skirt thereby locking the skirt to the neck finish of the vial. Squeezing of the bag may then cause liquid solution to be forced into the vial, and after the liquid solution and medication is mixed within the vial, the mixture may be returned to the flexible bag via suction created when squeezing of the bag is released and/or with gravity.

BRIEF DESCRIPTION OF THE DRAWINGS

Various features of the embodiments described in the following detailed description can be more fully appreciated when considered with reference to the accompanying figures, wherein the same numbers refer to the same elements.

DETAILED DESCRIPTION

For simplicity and illustrative purposes, principles of embodiments are described below by referring primarily to examples thereof. In the following description, numerous specific details are set forth to provide a thorough understanding of the embodiments. It will be apparent to one of ordinary skill in the art that the embodiments may be practiced without limitation to these specific details. In some instances, well known methods and structures have not been described in detail so as not to unnecessarily obscure the embodiments.

Embodiments are disclosed herein that provide an efficient and time consuming manner of delivering a medication to a liquid solution contained within a flexible bag and for subsequent use in a medical procedure, for instance, a dialysis treatment. These embodiments eliminate the delay in waiting for a medication to be added to a fresh supply of solution such as conventionally performed in a clean room, IV room, or like sterile environment, yet still enables sterility to be maintained during the transfer of the medication or like substance into the bag, for instance, in a patient treatment room where a dialysis session is to take place. These embodiments also provide a relatively easy process for adding a medication or like substance to a fresh supply of medical liquid solution to enable the process to be readily performed by patients and/or caregivers of patients with minimal training and require the use of less supplies and materials.

Figure 1:
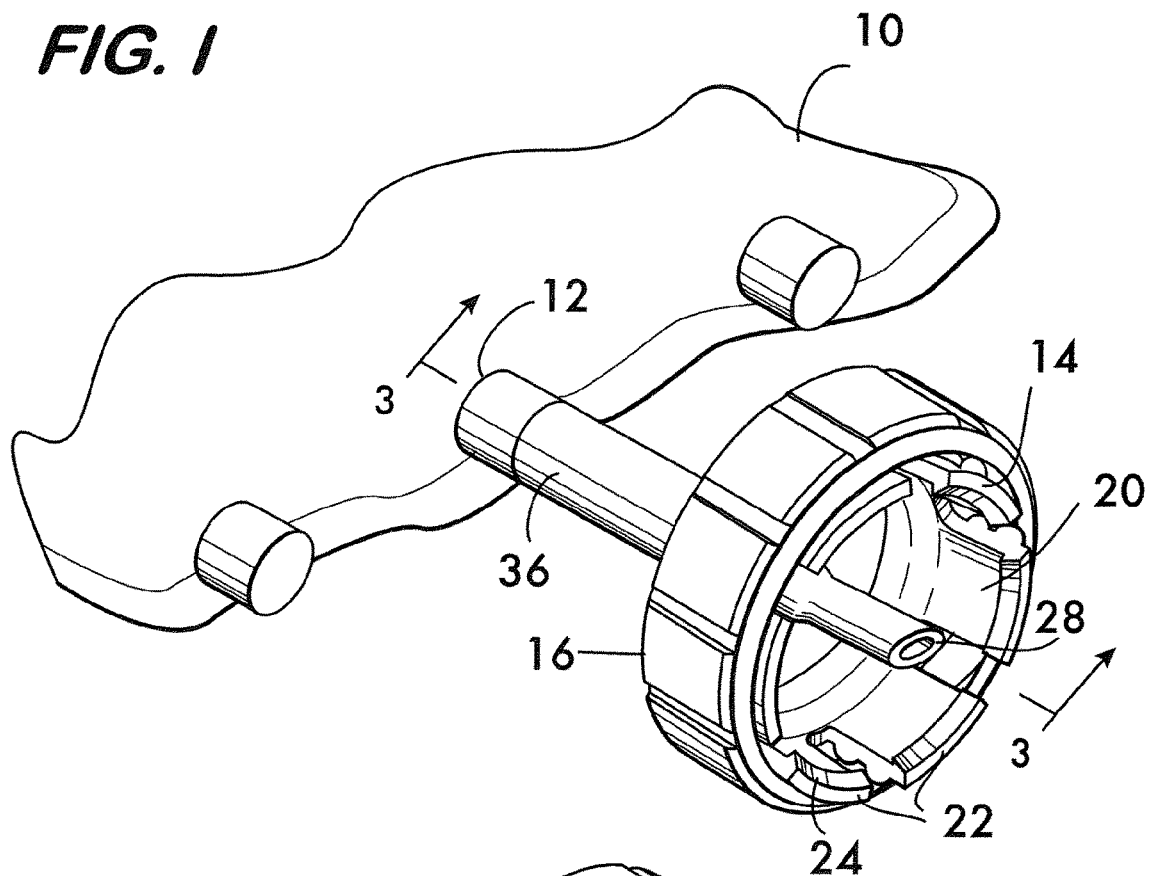
FIG. 1 is a perspective view of an adapter, locking ring, and a part of a flexible bag from which the adapter extends in accordance to an embodiment.

A part of a flexible bag 10, such as a dialysate bag containing a fresh supply of dialysate solution, is shown in FIG. 1. The bag 10 may be provided with a port 12 to which an adapter or vial interconnection device 14 communicates and/or is integrally provided. The adapter 14 is configured to engage about a neck finish of a vial and to be positively locked thereto with a locking device or ring 16. The bag 10 may also include additional ports, such as an output port through which the liquid solution exits the bag 10 during a medical treatment.

Figure 5:
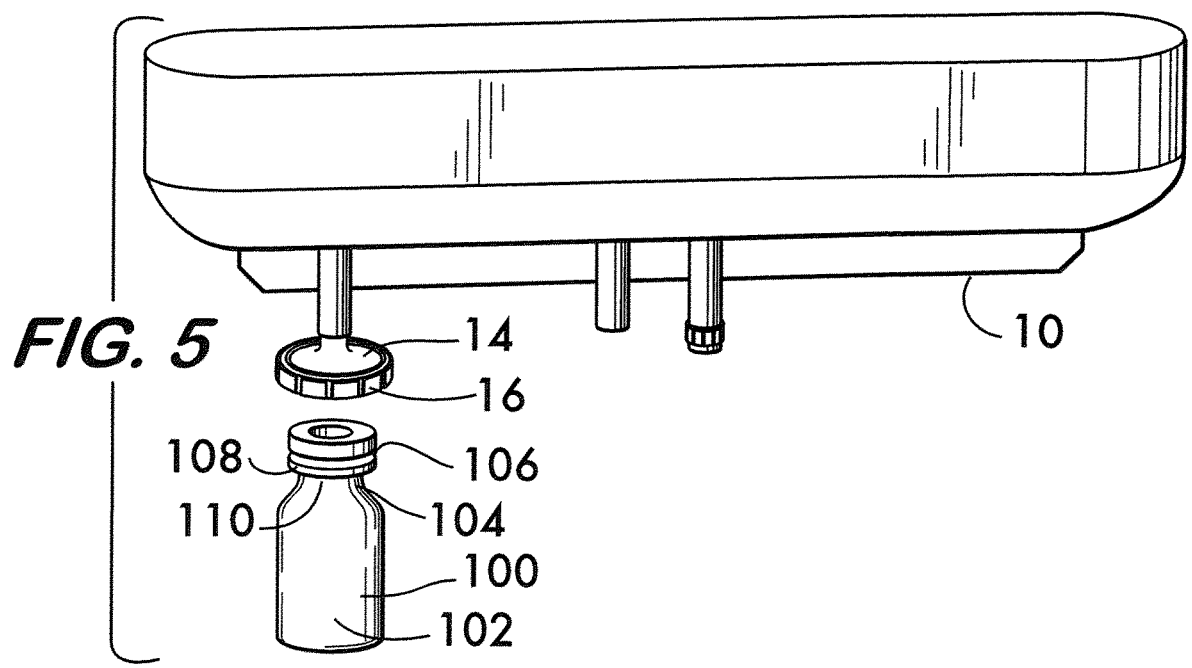
FIG. 5 is a perspective view of an end section of a flexible bag having an adapter and disconnected relative to a separate vial in accordance to an embodiment.
Figure 6:
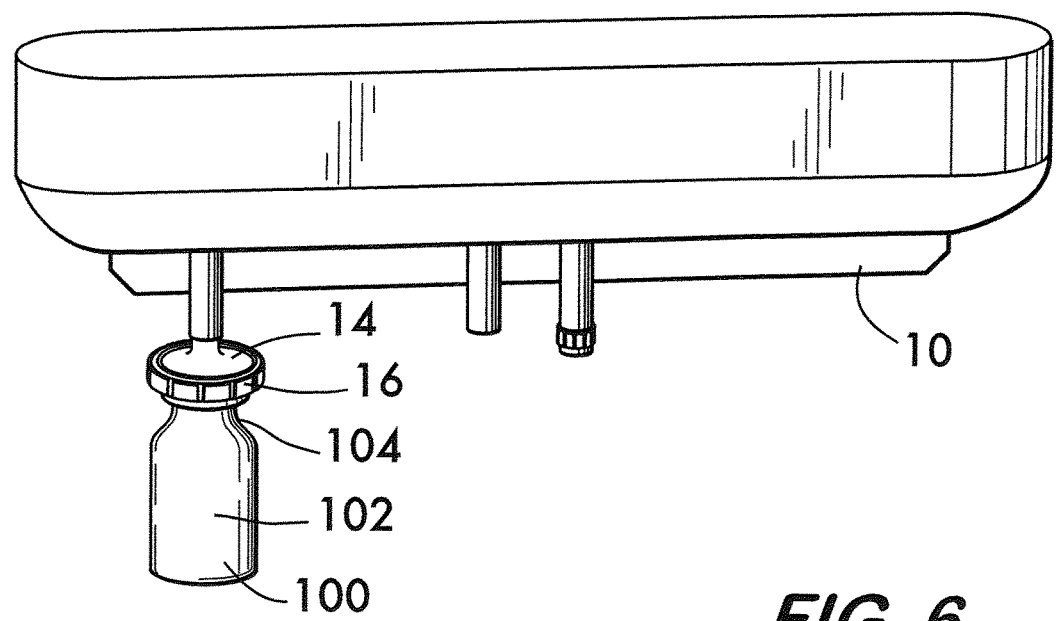
FIG. 6 is a perspective view of the end section of the flexible bag of FIG. 5 in which the adapter is connected and locked to the vial.

By way of example and not by way of limitation, a typical vial 100 may be provided having a 20 mL or other internal capacity. The vial 100 may be made of glass, rigid plastic or other material and may have a generally cylindrical or other-shaped hollow body 102 for containing a medication or other substance in a powder or liquid form. See FIGS. 5 and 6 for an example of a vial 100. An example of a medication contained by the vial 100 is an antibiotic.

The vial 100 has a relatively narrow throat 104 forming by a neck finish 106. The neck finish 106 defines a mouth of the vial in which a stopper or the like is provided to seal the medication within the vial 100. The exterior portion of the neck finish 106 may include an outwardly extending neck ring 108 or other outwardly extending structure. The significance of the neck ring 108 or the like of the neck finish 106 is that it provides an underside surface 110 about which the adapter 14 can be latched to positively grip the neck finish 106.

The adapter 14 of the bag 10 has a generally cap-like structure intended to be mounted over the neck finish 106 of the vial 100. Thus, the adapter 14 includes a disk-shaped upper wall 18 for extending over, engaging, and/or covering the mouth and/or stopper of the vial 100 and a relatively annular skirt 20 extending from a periphery of the upper wall 18. The skirt 20 is intended to snap onto and about the neck finish 106 of the vial 100. Thus, the shape and size of the upper wall 18 and skirt 20 of the adapter 14 are not limited and may be provided in any shape and size configured to correspond to the shape and size of the vial to be connected to the bag 10.

Figure 2:
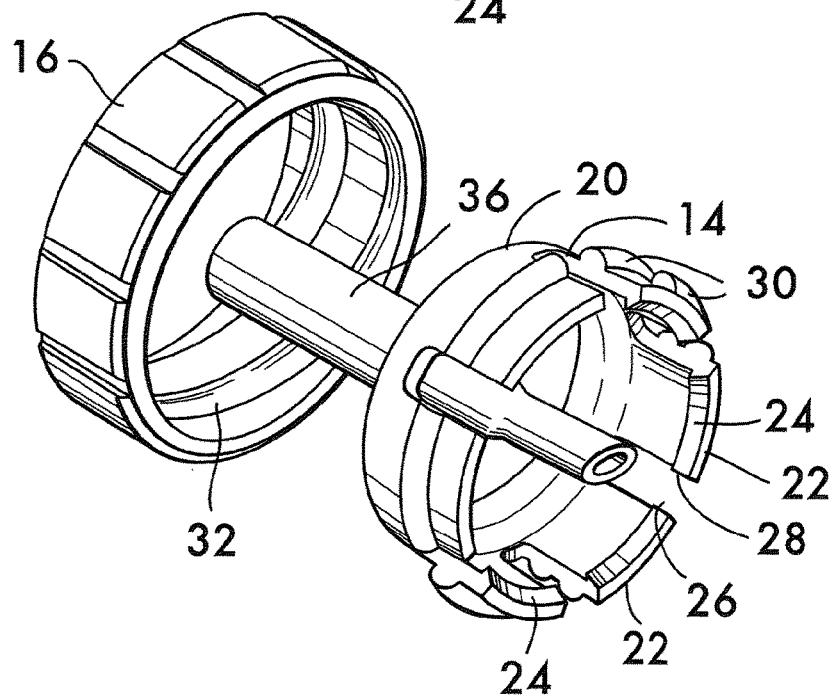
FIG. 2 is a perspective view of the adapter and locking ring in a disengaged condition in accordance to an embodiment.

As best shown in FIG. 2, the skirt 20 includes an array of separate, circumferentially spaced-apart, generally arc-shaped sections or fingers 22 each having a free end with an in-turned flange 24. Open slots 26 are formed and located between each pair of adjacent sections 22 to permit the sections 22 to spread apart in a radially outward expanded condition of the skirt 20 so that the in-turned flanges 24 can extend beyond the neck finish 106 and/or neck ring 108 of the vial 100 and be located in a position to latch underneath the underside surface 110. After the sections 22 are spread apart in an expanded condition and the neck finish 106 is fully received within the skirt 20, each section 22 automatically and resiliently returns to its normal position thereby positioning the in-turned flanges 24 below the neck ring 108 of the vial 100. In this condition, the flanges 24 latch the skirt 20 to neck finish 106 and thereby connect the adapter 14 to the vial 100.

Figure 3:
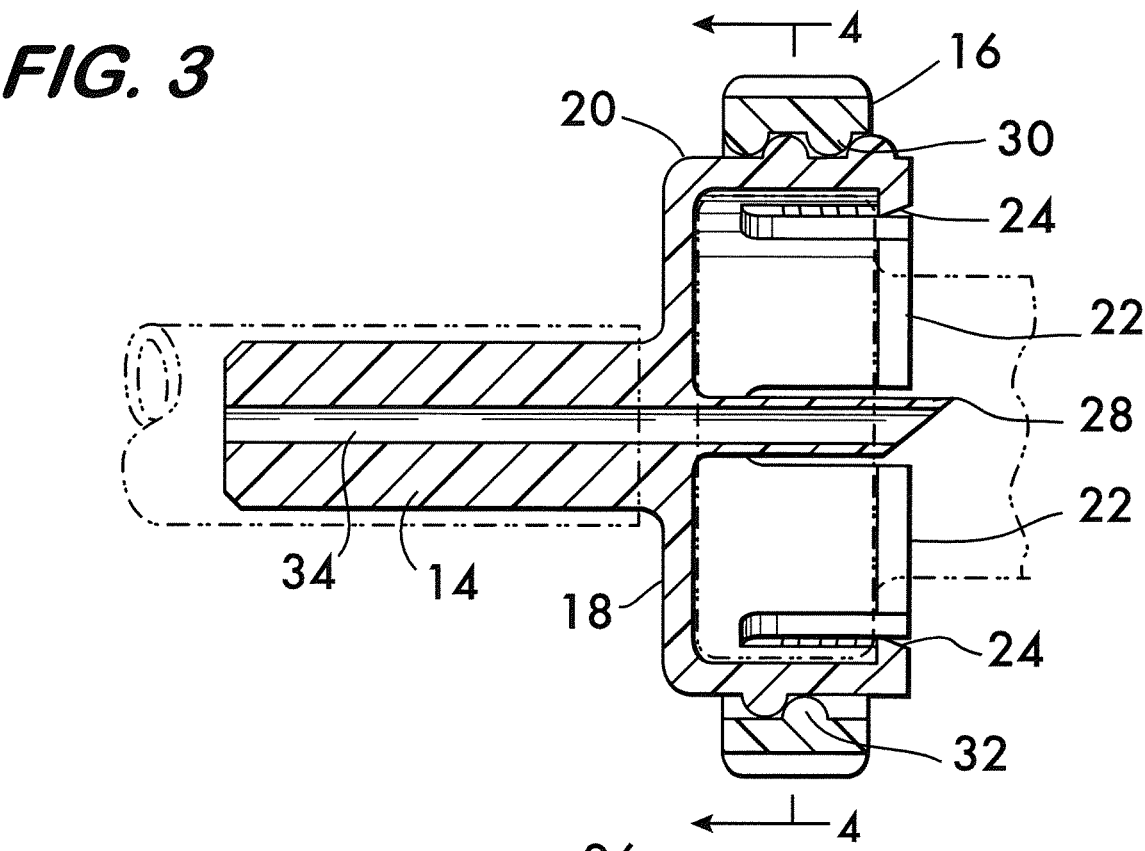
FIG. 3 is a cross-sectional view along line 3-3 of FIG. 1 showing the locking ring in a locked position on the adapter in accordance to an embodiment.
Figure 4:
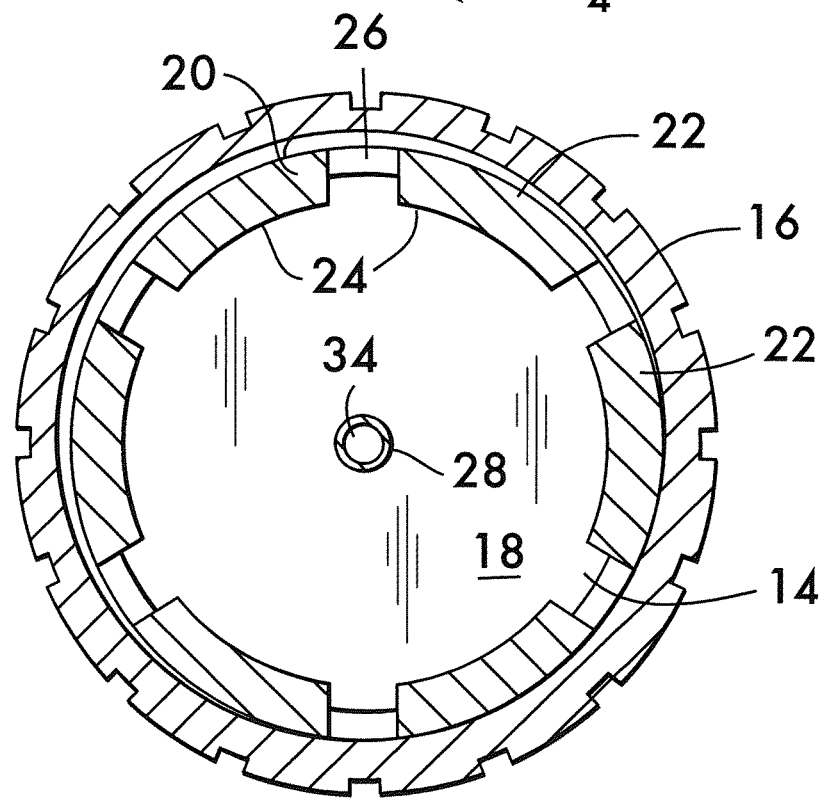
FIG. 4 is a cross-sectional view along line 4-4 of FIG. 3.

Unintended disconnection of the vial from the adapter described above is possible, for instance, when the bag 10 is squeezed as discussed below or during use in a medical treatment. Thus, for purposes of ensuring that the vial 100 does not become disengaged with the adapter 14, the adapter 14 includes a locking device or ring 16. For example, the skirt 20 and locking ring 16 may each include a complementary set of spiral threads, 30 and 32, respectively, that are able to be coupled together when the locking ring 16 is turned or rotated relative to the skirt 20. When the locking ring 16 is fully applied to and tightened about the adapter (i.e., when the locking ring is fully screwed onto the skirt 20), the locking ring 16 abuts against the outer surfaces of the sections 22 of the skirt 20 and thereby prevents the sections 22 from being spread apart in a radially outward manner. For instance, see FIGS. 3 and 4 which show the locking position of the locking ring 16 on the adapter 14. In this condition, the adapter 14 having been mounted on the neck finish 106 of the vial 100 is unable to be released from the vial and is securely and tightly connected thereto without concern of any unwanted separation, even when significant pressure is intentionally applied to the flexible bag 10.

The adapter 14 includes a relatively sharp-tipped cannula 28 extending from the upper wall 18 of the adapter 14 and centrally between the sections 22 of the skirt 20. Thus, when the skirt 20 of the adapter 14 is applied about a neck finish of a vial, the cannula 28 penetrates into and through a stopper provided in the mouth of the vial and gains entry within the interior of the vial. A hollow channel 34 extends through the cannula 30, the upper wall 18, and an opposite end 36 of the adapter 14 in communication with the interior of the bag 10. Thus, the hollow channel 34 provides a flow path between the bag 10 and connected vial 100, and the upper wall 18, skirt 20, and locking ring 16 ensure a fluid-tight seal between the bag 10 and the vial 100.

Accordingly, when a medication or like substance, such as an antibiotic in powder or liquid form, is desired to be added to the liquid solution contained within the flexible bag 10, a user may grip the adapter 14 in one hand and ensure that the locking ring 16 is sufficiently disengaged with the skirt 20 to permit the sections 22 of the skirt 20 to be able to spread apart as needed to accommodate a neck finish and/or neck ring of a vial. The adapter 14 may be held in a position above the fluid level contained within the bag, a sealing cap (not shown) provided on the cannula 28 (i.e., for closing the channel 32 of the adapter 14) may be removed, and the cannula may be wiped clean to ensure sterility. A vial 100 having a stopper located in the mouth of the vial may be held in the opposite hand of the user.

The adapter 14 may then be forced onto the neck finish 106 of the vial 100 via a snapping motion during which the sections 22 of the skirt 20 spread outwardly to accommodate the neck ring 108 of the vial 100 and then automatically and resiliently return inward to their normal original position whereby the in-turned flanges 24 extend beneath the neck ring 108 of the vial 100 thereby latching the adapter 14 to the neck finish 106. Thereafter, the locking ring 16 may be turned relative to the skirt 20 so that the locking ring 16 advances over the sections 22 of the skirt 20 to a locking position that prevents the sections 22 from unwanted outward deflection. In this condition, the adapter 14 is reliably locked to the neck finish 106 of the vial 100 and the vial cannot be released.

For purposes of mixing the liquid solution in the bag 10 with the medication or like substance contained in the vial 100, the bag 10 may be squeezed to force liquid solution contained within the bag 10 through channel 34 defined by the adapter 14 into the vial 100. The vial 100 may then be shaken to thoroughly mix the solution with the medicine and then the mixture may be caused to flow into the bag through channel 34 by the forces of suction created by releasing any squeezing of the bag 10 and/or by gravity by positioning the vial 100 above the bag 10.

After the mixture has been received within the bag 10, the bag 10 is ready for use. For example, the bag may contain dialysate with an added antibiotic and may be attached to a dialysate machine so that the dialysate with added antibiotic may be caused to flow through a dialyzer. The location of the adapter 14 on the bag 10 may be such that when the bag is connected to the dialysis machine the adapter 14 is located at the top of the bag 10 preventing flow of the solution into the vial. Also, the vial 100 may remain attached to the bag 10 during dialysis treatment for safety purposes providing a clear indication as to the fact that the contents of the vial have already been added to the bag. Alternatively, the vial may be removed from the bag and the adapter sealed close. In this case, the sealing ring 16 needs to be unscrewed relative to the skirt to pen' it the sections of the skirt to unsnap from the neck finish of the vial.

After use, the adapter 14, bag 10 as well as the vial may be readily recycled and/or properly discarded. For instance, the adapter 14 may be made of a recyclable plastic material or the like.

While the principles of the invention have been described above in connection with specific devices, assemblies, and methods, it is to be clearly understood that this description is made only by way of example and not by way of limitation. For instance, while a dialysate bag added with an antibiotic in powder form for use in a dialysis machine is described above, the bag may contain any type of solution and be added within any type of medicine, drug, or other additive or agent in any form. Also, while an annular shaped skirt and locking ring are shown, other shaped skirts and locking devices that are not circular may be utilized. Still further, the locking device may be secured to the skirt with mechanisms other than spiral threads, such as by friction, the use of a separate clip or band, or the like.

Thus, one of ordinary skill in the art will appreciate that various modifications and changes can be made without departing from the scope of the claims below. Accordingly, the specification and figures are to be regarded in an illustrative rather than a restrictive sense, and all such modifications are intended to be included within the scope of the present invention.

We claim:

1. An assembly for adding a medication to a liquid solution, comprising:
    a flexible bag (10) for containing a liquid solution, said flexible bag (10) having a first port (12) and at least one second port through which the liquid solution may be caused to flow;
    an adapter (14) integral with flexible bag (10) and extending from said first port (12) of said flexible bag (10), said adapter (14) having a skirt (20) with an array of spaced-apart, resilient sections (22) that enable the skirt (20) to engage and be latched to a neck finish of a separate vial containing a medication; and
    a locking device (16) securable about said skirt (20) in a locking position that prevents outward movement of said resilient sections (22), said locking device (16) being a locking ring that, when positioned in said locking position, encircles said resilient sections (22) of said skirt (20), said locking ring (16) and said skirt (20) having complementary threaded surfaces (30, 32) permitting said locking ring (16) to be screwed directly onto said skirt (20), and said locking ring (16) being captured between said flexible bag (10) and said adapter (14) including when said skirt (20) of said adapter (14) is not latched to a separate vial.

2. The assembly according to claim 1, wherein the skirt (20) is annular and each of the resilient sections (22) is arc-shaped and include an in-turned flange (24) for extending under an underside surface of a neck finish of a vial.

3. The assembly according to claim 2, wherein the adapter (14) includes an upper wall (18) from which the skirt (20) depends and a cannula (28) integral with and extending from the upper wall (18) for piercing a stopper of a vial.

4. The assembly according to claim 3, wherein said adapter (14) defines a channel (34) that extends continuously through the cannula (28) and the upper wall (18) and into said flexible bag (10).

5. The assembly according to claim 4, wherein said flexible bag (10) contains dialysate for use during dialysis.

6. An assembly for adding a medication to a liquid solution, comprising:
    a flexible bag (10) containing a liquid solution, said flexible bag (10) having a first port (12) and at least one second port through which the liquid solution may be caused to flow;
    a separate vial (100) containing a medication and having a neck finish (106) defining a mouth with a stopper;
    an adapter (14) integral with flexible bag (10) and extending from said first port (12) of said flexible bag (10) and having a skirt (20) with an array of spaced-apart, resilient sections (22) for engaging and resiliently snapping onto the neck finish (106) of the vial (100); and a locking device (16) securable about said skirt (20) in a locking position that prevents outward movement of said array of spaced-apart, resilient sections (22) of said skirt (20), said locking device (16) being a locking ring that, when positioned in said locking position, encircles said resilient sections (22) of said skirt (20);

said locking ring (16) and said skirt (20) having complementary spiral threads (30, 32) permitting said locking ring (16) to be advanced over said skirt (20) and rotated relative to said skirt (20) so as to be screwed directly onto said skirt (20); and said locking ring (16) being captured between said flexible bag (10) and said adapter (14) including when said skirt (20) of said adapter (14) is not engaged with the separate vial (100).

7. The assembly according to claim 6, wherein the skirt (20) is annular, the resilient sections (22) are circumferentially spaced apart, and each of the resilient sections (22) are arc-shaped and include an in-turned flange (24) for extending beneath an underside surface (110) of the neck finish (106) of the vial (100) to latch the adapter (14) to the vial (100).

8. The assembly according to claim 7, wherein the adapter (14) includes an upper wall (18) from which the skirt (20) depends and a cannula (28) extending from the upper wall (18) for piercing the stopper of the vial (100).

9. The assembly according to claim 8, wherein said adapter (14) defines a channel (34) that extends continuously through the cannula (28) from within the vial (100) and through the upper wall (18) of the adapter (14) and into said flexible bag (10).

10. The assembly according to claim 9, wherein said flexible bag (10) contains dialysate for use during dialysis and said vial (100) contains an antibiotic in a form of a powder or liquid.

11. A method of adding a medication to a liquid solution, comprising the steps of:

connecting an adapter (14) of a flexible bag (10) containing a liquid solution to a separate vial (100) containing a medication, the vial (100) having a neck finish (106) defining a mouth with a stopper, the flexible bag (10) having a first port (12) and at least one second port through which the liquid solution may be caused to flow, and the adapter (14) extending integrally from the first port (12) of the flexible bag (10), having a skirt (20) with an array of resilient sections (22) for engaging and resiliently snapping onto the neck finish (106) of the vial (100), and having a cannula (28) which pierces the stopper of the vial (100);

after said connecting step, securing a locking device (16) in a locking position about the skirt (20) such that the locking device (16) prevents outward movement of said array of resilient sections (22) of said skirt (20) thereby locking the skirt (20) to the neck finish (106) of the vial, the locking device (16) being a locking ring that, when positioned in the locking position, encircles and engages the array of resilient sections (22) of the skirt (20), the locking ring (16) and the skirt (20) of the adapter (14) having complementary spiral threads (30, 32) such that said securing step includes rotating the locking ring (16) relative to the skirt (20), and the locking ring (16) being captured between the flexible bag (10) and the adapter (14) including when the skirt (20) of the adapter (14) is not engaged with the vial; and after said securing step, squeezing the flexible bag (10) to cause an amount of the liquid solution contained in the flexible bag (10) to pass through a channel (34) extending through the adapter (14) and cannula (28) and into the vial (100);

mixing the liquid solution and medication within the vial (100) by shaking the vial (100) to form a mixture; and causing the mixture to pass through the adapter (14) and into the flexible bag (10).

12. The method according to claim 11, wherein the skirt (20) is annular, the array of resilient sections (22) are circumferentially spaced apart, and each of the resilient sections (22) are arc-shaped and include an in-turned flange (24) for extending beneath an underside surface (110) of the neck finish (106) of the vial (100) to latch the adapter (14) to the neck finish (106) of the vial (100).

13. The method according to claim 12, wherein, before said squeezing step, the flexible bag (10) contains dialysate and the vial (100) contains an antibiotic in a form of a powder or liquid.

* * * * *